US008709493B2

(12) United States Patent
Daniel et al.

(10) Patent No.: US 8,709,493 B2
(45) Date of Patent: *Apr. 29, 2014

(54) PLACENTAL TISSUE GRAFTS

(71) Applicant: Mimedx Group, Inc., Marietta, GA (US)

(72) Inventors: John Daniel, Woodstock, GA (US); Robert Tofe, Denver, CO (US); Randall Spencer, Acworth, GA (US); John Russo, Sarasota, FL (US)

(73) Assignee: Mimedx Group, Inc., Kennesaw, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/765,640

(22) Filed: Feb. 12, 2013

(65) Prior Publication Data

US 2013/0197665 A1    Aug. 1, 2013

Related U.S. Application Data

(63) Continuation of application No. 13/569,134, filed on Aug. 7, 2012, now Pat. No. 8,409,626, which is a continuation of application No. 12/428,908, filed on Apr. 23, 2009, now Pat. No. 8,323,701, which is a continuation of application No. 12/206,508, filed on Sep. 8, 2008, now Pat. No. 8,357,403.

(60) Provisional application No. 60/970,780, filed on Sep. 7, 2007, provisional application No. 60/986,665, filed on Nov. 9, 2007, provisional application No. 60/989,299, filed on Nov. 20, 2007.

(51) Int. Cl.
*A61K 35/50* (2006.01)

(52) U.S. Cl.
USPC .......................................................... 424/583

(58) Field of Classification Search
None
See application file for complete search history.

(56) References Cited

U.S. PATENT DOCUMENTS

| 4,361,552 | A | 11/1982 | Baur, Jr. |
| 4,446,234 | A | 5/1984 | Russo et al. |
| 4,846,165 | A | 7/1989 | Hare et al. |
| 5,197,976 | A | 3/1993 | Herweck et al. |
| 5,350,583 | A | 9/1994 | Yoshizato et al. |
| 5,612,028 | A | 3/1997 | Sackier et al. |
| 5,711,969 | A | 1/1998 | Patel et al. |
| 5,882,929 | A | 3/1999 | Fofonoff et al. |
| 5,885,619 | A | 3/1999 | Patel et al. |
| 5,955,110 | A | 9/1999 | Patel et al. |
| 5,968,096 | A | 10/1999 | Whitson et al. |
| 5,997,575 | A | 12/1999 | Whitson et al. |
| 6,143,315 | A | 11/2000 | Wang et al. |
| 6,146,414 | A | 11/2000 | Gelman |
| 6,152,142 | A | 11/2000 | Tseng |
| 6,326,019 | B1 | 12/2001 | Tseng |
| 6,379,710 | B1 | 4/2002 | Badylak |
| 6,398,797 | B2 | 6/2002 | Bombard et al. |
| 6,544,289 | B2 | 4/2003 | Wolfinbarger et al. |
| 7,045,148 | B2 | 5/2006 | Hariri |
| 7,049,139 | B2 | 5/2006 | Tan et al. |
| 7,244,444 | B2 | 7/2007 | Bates |
| 7,311,904 | B2 | 12/2007 | Hariri |
| 7,311,905 | B2 | 12/2007 | Hariri |
| 7,413,734 | B2 | 8/2008 | Mistry et al. |
| 8,323,701 | B2 | 12/2012 | Daniel et al. |
| 8,357,403 | B2 | 1/2013 | Daniel et al. |
| 8,372,438 | B2 | 2/2013 | Daniel et al. |
| 8,372,439 | B2 | 2/2013 | Daniel et al. |
| 8,409,626 | B2 | 4/2013 | Daniel et al. |
| 2002/0034757 | A1 | 3/2002 | Cubicciotti |
| 2002/0039788 | A1 | 4/2002 | Isseroff et al. |
| 2003/0032179 | A1 | 2/2003 | Hariri |
| 2003/0135284 | A1 | 7/2003 | Crouch et al. |
| 2003/0187515 | A1 | 10/2003 | Hariri et al. |
| 2003/0235909 | A1 | 12/2003 | Hariri et al. |
| 2004/0028660 | A1 | 2/2004 | Hariri et al. |
| 2004/0039453 | A1 | 2/2004 | Anderson et al. |
| 2004/0048796 | A1 | 3/2004 | Hariri et al. |
| 2004/0057938 | A1 | 3/2004 | Ghinelli |
| 2004/0126878 | A1 | 7/2004 | Ramos et al. |

(Continued)

FOREIGN PATENT DOCUMENTS

CN    2006/1015653    12/2007
CN    101088479       12/2007

(Continued)

OTHER PUBLICATIONS

Rodriguez-Ares et al, Acta Ophthalmologica, 2009, vol. 87, pp. 396-403.*

(Continued)

*Primary Examiner* — Allison Ford
(74) *Attorney, Agent, or Firm* — Foley & Lardner LLP

(57) ABSTRACT

Described herein are tissue grafts derived from the placenta. The grafts are composed of at least one layer of amnion tissue where the epithelium layer has been substantially removed in order to expose the basement layer to host cells. By removing the epithelium layer, cells from the host can more readily interact with the cell-adhesion bio-active factors located onto top and within of the basement membrane. Also described herein are methods for making and using the tissue grafts. The laminin structure of amnion tissue is nearly identical to that of native human tissue such as, for example, oral mucosa tissue. This includes high level of laminin-5, a cell adhesion bio-active factor show to bind gingival epithelia-cells, found throughout upper portions of the basement membrane.

6 Claims, 8 Drawing Sheets

(56) References Cited

U.S. PATENT DOCUMENTS

| | | |
|---|---|---|
| 2004/0171147 A1 | 9/2004 | Hariri |
| 2004/0219136 A1 | 11/2004 | Hariri |
| 2004/0265293 A1 | 12/2004 | Crowe et al. |
| 2005/0026279 A1 | 2/2005 | Tseng et al. |
| 2005/0107876 A1 | 5/2005 | Kim et al. |
| 2005/0118715 A1 | 6/2005 | Hariri et al. |
| 2005/0148034 A1 | 7/2005 | Hariri et al. |
| 2006/0004189 A1 | 1/2006 | Gandy |
| 2006/0147492 A1 | 7/2006 | Hunter et al. |
| 2006/0153928 A1 | 7/2006 | Kinoshita et al. |
| 2006/0222634 A1 | 10/2006 | Clarke et al. |
| 2006/0228339 A1 | 10/2006 | Wang |
| 2007/0020225 A1 | 1/2007 | Abramson et al. |
| 2007/0021704 A1 | 1/2007 | Hariri et al. |
| 2007/0021762 A1 | 1/2007 | Liu et al. |
| 2007/0031471 A1 | 2/2007 | Peyman |
| 2007/0038298 A1 | 2/2007 | Sulner et al. |
| 2007/0071740 A1 | 3/2007 | Tseng et al. |
| 2007/0134210 A1 | 6/2007 | Heidaran |
| 2007/0154515 A1 | 7/2007 | Johnson et al. |
| 2007/0190042 A1 | 8/2007 | Edinger et al. |
| 2007/0218039 A1 | 9/2007 | Devi et al. |
| 2007/0231401 A1 | 10/2007 | Tseng et al. |
| 2007/0254005 A1 | 11/2007 | Pathak et al. |
| 2007/0254013 A1 | 11/2007 | Taguchi et al. |
| 2007/0269791 A1 | 11/2007 | Takami et al. |
| 2007/0292401 A1 | 12/2007 | Harmon et al. |
| 2008/0032401 A1 | 2/2008 | Edinger et al. |
| 2008/0044848 A1 | 2/2008 | Heidaran |
| 2008/0046095 A1 | 2/2008 | Daniel |
| 2008/0069895 A1 | 3/2008 | Liu et al. |
| 2008/0181935 A1 | 7/2008 | Bhatia et al. |
| 2008/0213389 A1 | 9/2008 | Lelkes et al. |
| 2008/0248005 A1 | 10/2008 | Phan |
| 2012/0078378 A1 | 3/2012 | Daniel et al. |
| 2012/0294910 A1 | 11/2012 | Daniel et al. |
| 2013/0129836 A1 | 5/2013 | Daniel et al. |

FOREIGN PATENT DOCUMENTS

| | | |
|---|---|---|
| EP | 0 773 033 A1 | 5/1997 |
| FR | 2892311 | 4/2007 |
| JP | 08-266613 | 10/1996 |
| WO | WO-2005/007835 A1 | 1/2005 |
| WO | WO-2006/129673 | 12/2006 |
| WO | WO-2009/033160 | 3/2009 |
| WO | WO-2009/132186 | 10/2009 |

OTHER PUBLICATIONS

Bhatia, et al., "The Mechanism of Cell Interaction and Response on Decellularized Human Amniotic Membrane: Implications in Wound Healing," http://www.woundsresearch.com/article/7614, (2007), 19(8):1-24.

Ebihara, et al., "The Functions of Exogenous and Endogenous Laminin-5 on Corneal Epithelial Cells," Exp. Eye Res., (2000), 71:69-79.

U.S. Appl. No. 60/970,780, filed Sep. 14, 2008, Tofe.

U.S. Appl. No. 60/986,665, filed Nov. 9, 2007, Daniel.

U.S. Appl. No. 60/989,299, filed Nov. 20, 2007, Tofe, et al.

Extended European Search Report dated Nov. 27, 2012 in related European Application Serial No. 08829350.1.

Fukuda, et al., "Differential Distribution of Subchains of the Basement Membrane Components Type IV Collagen and Laminin Among the Amniotic Membrane, Cornea, and Conjunctiva," Cornea, (1999), 18:73-79.

Hao, et al., "Identification of Antiangiogenic and Antiinflammatory Proteins in Human Amniotic Membrane," Cornea, (2000), 19(3):348-352.

International Search Report and Written Opinion dated Nov. 13, 2008 in related PCT Application No. PCT/US08/75608.

Koizumi, et al., "Growth Factor mRNA and protein in preserved human amniotic membrane," Current Eye Research, (2000), 20(3):173-177.

Niknejad, et al., "Properties of the Amniotic Membrane for Potential Use in Tissue Engineering," European Cells and Materials, (2008), 15:88-99.

Pakkala, et al., "Function of Laminins and Laminin-Binding Integrins in Gingival Epithelial Cell Adhesion," J. Periodontol., (2002), 73:709-719.

Park, et al., "Healing of a porcine burn wound dressed with human and bovine amniotic membranes," Wound Rep. Reg., (2008), 16:520-528.

Rinastiti, et al., "Histological evaluation of rabbit gingival wound healing transplanted with human amniotic membrane," Int. J. Oral Maxillofac. Surg., (2006), 35:247-251.

Takashima, et al., "Characterization of laminin isoforms in human amnion," Tissue and Cell, (2008), 40:75-81.

Talmi, et al., "Antibacterial Properties of Human Amniotic Membranes," Placenta, (1991), 12:285-288.

Toda, et al., "The Potential of Amniotic Membrane/Amnion-Derived Cells for Regeneration of Various Tissues," J. Pharmacol. Sci., (2007), 105:215-228.

\* cited by examiner

Tissue Check-In Form

FIG. 2

Tissue ID: _____ Date: _____ Time: _____

Inspect Shipment:

| | | |
|---|---|---|
| Is the shipping container sealed and intact? | ☐ Yes | ☐ No |
| Is ice or other coolant present and is contents cool? | ☐ Yes | ☐ No |
| Is donor paperwork present? | ☐ Yes | ☐ No |
| Does donor number on paperwork and tissue ID correspond? | ☐ Yes | ☐ No |

Log Tissue into Refrigerator Log:

| | | |
|---|---|---|
| Complete | ☐ Yes | ☐ No |

Shipment Accepted: ☐ Accept
☐ Reject

By: _____ Date: _____

Reason for Rejection: _____

Comments: _____

Signature: _____ Date: _____ Time: _____

Raw Tissue Assessment Form　　　　　　　　　　FIG. 3

Donor: _____　　Date: _____

Inspect tissue:

| | | |
|---|---|---|
| Is the tissue discolored? | ☐ Yes | ☐ No |
| Is there any debris present? | ☐ Yes | ☐ No |
| Does the tissue present any unacceptable odor? | ☐ Yes | ☐ No |
| Tissue shows signs of damage? | ☐ Yes | ☐ No |

*If "Yes" to any questions above, sketch diagram of tissue including notable features:*

Tissue is acceptable for processing:　　　☐ Pass　　　☐ Fail

Size of tissue:　　　_____ CM X _____ CM

Comments: _____

Tissue has been assessed according to SOP Raw Tissue Assessment (SB-0205-P) and deemed acceptable for processing.

Signature: _____　　Date: _____

Dehydration Process Form

FIG. 4

| Load Technician: | | Start Date: | / / |
|---|---|---|---|
| | | Start Time: | : |
| Confirm Oven Set Temperature @ 45°C ☐ | | | |
| Enter all Donor Numbers Below | | | |

| 01 | |
|---|---|
| 02 | |
| 03 | |
| 04 | |
| 05 | |
| 06 | |
| 07 | |
| 08 | |
| 09 | |
| 10 | |

| Quantity of Tissues Dried: | | Finish Time: | : |
|---|---|---|---|
| | | Finish Date: | / / |
| | Total Dehydration Time: | hours | minutes |
| Residual Moisture Samples Prepared: ☐ | | | |
| Unload Technician: | | | |
| QA Review: | | Date: | |

PLACENTAL TISSUE GRAFTS

CROSS REFERENCE TO RELATED APPLICATIONS

This application is a continuation application of U.S. application Ser. No. 13/569,134, filed on Aug. 7, 2012; which is a continuation application of U.S. application Ser. No. 12/428,908, filed on Apr. 23, 2009, now U.S. Pat. No. 8,323,701, issued on Dec. 4, 2012; which is a continuation application of U.S. application Ser. No. 12/206,508, filed on Sep. 8, 2008, now U.S. Pat. No. 8,357,403, issued on Jan. 22, 2013; which claims priority upon U.S. provisional application Ser. Nos. 60/970,780, filed Sep. 7, 2007; 60/986,665, filed Nov. 9, 2007; and 60/989,299, filed Nov. 20, 2007. Each application is hereby incorporated by reference in its entirety for all of its teachings.

BACKGROUND

Human placental membrane (e.g. amniotic membrane or tissue) has been used for various types of reconstructive surgical procedures since the early 1900s. The membrane serves as a substrate material, more commonly referred to as a biological dressing or patch graft. Such a membrane has also been used widely for ophthalmic procedures. Typically, such membrane is either frozen or dried for preservation and storage until needed for surgery.

Such placental tissue is typically harvested after an elective Cesarean surgery. The placenta is composed of the umbilical cord and amniotic sac. The amniotic sac, commonly referred to as the amniotic membrane, has two primary layers of tissue, amnion and chorion. Amnion tissue is innermost layer of the amniotic sac and in direct contact with the amniotic fluid. The amniotic sac contains the amniotic fluid and protects the fetal environment. Histological evaluation indicates that the membrane layers of the amnion consist of single layer of epithelium cells, thin reticular fibers (basement membrane), a thick compact layer, and fibroblast layer. The fibrous layer of amnion (i.e., the basement membrane) contains collagen types IV, V, and VII, and cell-adhesion bio-active factors including fibronectin and laminins.

Amnion tissue provides unique grafting characteristics when used for surgical procedures, including providing a matrix for cellular migration/proliferation, providing a natural biological barrier, are non-immunogenic, and contains numerous bio-active molecules, which can be used as a membrane to assist in tissue regeneration and improved healing outcomes in numerous applications. The membrane has the capability to self-adhere or, in the alternative, is susceptible of being fixed in place using different techniques including fibrin glue or suturing. Such grafts, when properly prepared, can be stored at room temperature for extended periods of time, without need for refrigeration or freezing, until needed for a surgical procedure.

Known clinical procedures or applications for such amnion grafts include ocular reconstruction, burns, anti-adhesion applications, barrier membranes, and general wound care. Described herein are membranes utilizing amnion tissue as building blocks to build membranes well suited for use in a variety of application such as, for example, perioplastic surgery and other surgical applications involving human mucosa tissue. The grafts and methods described herein utilize these biological molecules to enhance the performance of the amniotic membrane.

SUMMARY OF INVENTION

Described herein are tissue grafts derived from the placenta. The grafts are composed of at least one layer of amnion tissue where the epithelium layer has been substantially removed in order to expose the basement layer to host cells. By removing the epithelium layer, cells from the host can more readily interact with the cell-adhesion bio-active factors located onto top and within of the basement membrane. Also described herein are methods for making and using the tissue grafts. The laminin structure of amnion tissue is nearly identical to that of native human tissue such as, for example, oral mucosa tissue. This includes high level of laminin-5, a cell adhesion bio-active factor show to bind gingival epithelia-cells, found throughout upper portions of the basement membrane. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

FIG. 2 is an exemplary tissue check-in form used with the tissue grafts described herein.

FIG. 3 is an exemplary raw tissue assessment form used with the tissue grafts described herein.

FIG. 4 is an exemplary dehydration process form used with the tissue grafts described herein.

DETAILED DESCRIPTION

Before the present articles and methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a bioactive agent" includes mixtures of two or more such agents, and the like.

"Optional" or "optionally" means that the subsequently described event or circumstance can or cannot occur, and that the description includes instances where the event or circumstance occurs and instances where it does not. For example, the phrase "optionally cleaning step" means that the cleaning step may or may not be performed.

Titles or subtitles may be used in the specification for the convenience of a reader, which are not intended to influence the scope of the present invention. Additionally, some terms used in this specification are more specifically defined below.

I. Tissue Grafts and Methods for Making Thereof

Described herein are tissue grafts and methods of making and using thereof. In general, the tissue grafts are multilayered systems composed of one or more membranes laminated to a base amnion, where the epithelium layer of the base amnion has been substantially removed. In one aspect, the process for preparing the amnion and removing the epithelium layer involves (a) obtaining a placenta from a subject, wherein the placenta comprises an amniotic membrane layer and a chorion tissue layer;
(b) separating the chorion tissue layer from the amnion layer, wherein the amnion comprises epithelium cells adjacent to a basement membrane;
(d) removing substantially all of the epithelium cells to expose the basement membrane of the amnion;
(e) mounting the first membrane onto a surface of a drying fixture;
(f) mounting one or more additional membranes on the first membrane to produce a layered tissue graft; and
(g) dehydrating the layered tissue graft on the drying fixture.

Figure 1:
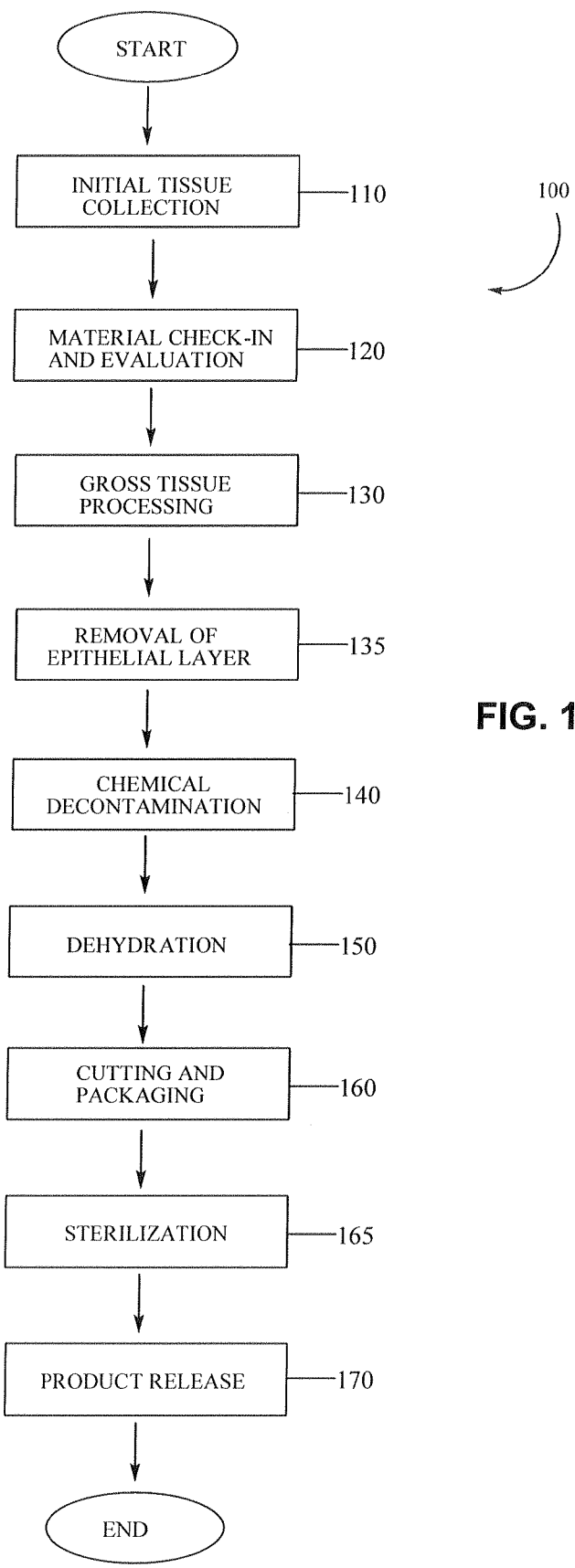
FIG. 1 is an overview flow chart of the process for making the tissue grafts described herein.

FIG. 1 depicts an overview (100) of the steps to harvest, process, and prepare placental material for later use as a tissue graft is disclosed. More detailed descriptions and discussion regarding each individual step will follow. Initially, the placenta tissue is collected from a consenting patient following an elective Cesarean surgery (step 110). The material is preserved and transported in conventional tissue preservation manner to a suitable processing location or facility for check-in and evaluation (step 120). Gross processing, handling, and separation of the tissue layers then takes place (step 130). After the epithelium layer is substantially removed from the amnion to expose the base membrane (step 135), acceptable tissue is then decontaminated (step 140), dehydrated (step 150), cut and packaged (step 160), tissue is radiological terminal sterilized using gamma radiation (step 165), and released (step 170) to the market for use by surgeons and other medical professionals in appropriate surgical procedures and for wound care. Each step is described in detail below.

Initial Tissue Collection (Step 110)

The recovery of placenta tissue originates in a hospital, where it is collected during a Cesarean section birth. The donor, referring to the mother who is about to give birth, voluntarily submits to a comprehensive screening process designed to provide the safest tissue possible for transplantation. The screening process preferably tests for antibodies to the human immunodeficiency virus type 1 and type 2 (anti-HIV-1 and anti-HIV-2), hepatitis B surface antigens (HBsAg), antibodies to the hepatitis C virus (anti-HCV), antibodies to the human T-lymphotropic virus type I and type II (anti-HTLV-I and anti-HTLV-II), CMV, and syphilis, using conventional serological tests. The above list of tests is exemplary only, as more, fewer, or different tests may be desired or necessary over time or based upon the intended use of the grafts, as will be appreciated by those skilled in the art.

Based upon a review of the donor's information and screening test results, the donor will either be deemed acceptable or not. In addition, at the time of delivery, cultures are taken to determine the presence of bacteria, for example, *Clostridium* or *Streptococcus*. If the donor's information, screening tests, and the delivery cultures are all satisfactory (i.e., do not indicate any risks or indicate acceptable level of risk), the donor is approved by a medical director and the tissue specimen is designated as initially eligible for further processing and evaluation.

Human placentas that meet the above selection criteria are preferably bagged in a saline solution in a sterile shipment bag and stored in a container of wet ice for shipment to a processing location or laboratory for further processing.

If the placenta tissue is collected prior to the completion or obtaining of results from the screening tests and delivery cultures, such tissue is labeled and kept in quarantine. The tissue is approved for further processing only after the required screening assessments and delivery cultures, which declare the tissue safe for handling and use, are satisfied and obtains final approval from a medical director.

Material Check-in and Evaluation (Step 120)

Upon arrival at the processing center or laboratory, the shipment is opened and verified that the sterile shipment bag/container is still sealed and in the coolant, that the appropriate donor paperwork is present, and that the donor number on the paperwork matches the number on the sterile shipment bag containing the tissue. The sterile shipment bag containing the tissue is then stored in a refrigerator until ready for further processing. All appropriate forms, including a tissue check-in form, such as that shown in FIG. 2, are completed and chain of custody and handling logs (not shown) are also completed.

Gross Tissue Processing (Step 130)

When the tissue is ready to be processed further, the sterile supplies necessary for processing the placenta tissue further are assembled in a staging area in a controlled environment and are prepared for introduction into a controlled environment. If the controlled environment is a manufacturing hood, the sterile supplies are opened and placed into the hood using conventional sterile technique. If the controlled environment is a clean room, the sterile supplies are opened and placed on a cart covered by a sterile drape. All the work surfaces are covered by a piece of sterile drape using conventional sterile techniques, and the sterile supplies and the processing equipments are placed on to the sterile drape, again using conventional sterile techniques.

Processing equipment is decontaminated according to conventional and industry-approved decontamination procedures and then introduced into the controlled environment. The equipment is strategically placed within the controlled environment to minimize the chance for the equipment to come in proximity to or is inadvertently contaminated by the tissue specimen.

Next, the placenta is removed from the sterile shipment bag and transferred aseptically to a sterile processing basin within the controlled environment. The sterile basin contains hyper-isotonic saline solution (e.g., 18% NaCl) that is at room or near room temperature. The placenta is gently massaged to help separate blood clots and to allow the placenta tissue to reach room temperature, which will make the separation of the amnion and chorion layers from each other, as discussed hereinafter, easier. After having warmed up to the ambient temperature (after about 10-30 minutes), the placenta is then removed from the sterile processing basin and laid flat on a processing tray with the amniotic membrane layer facing down for inspection.

The placenta tissue is examined and the results of the examination are documented on a "Raw Tissue Assessment Form" similar to that shown in FIG. 3. The placenta tissue is examined for discoloration, debris or other contamination, odor, and signs of damage. The size of the tissue is also noted. A determination is made, at this point, as to whether the tissue is acceptable for further processing.

Next, if the placenta tissue is deemed acceptable for further processing, the amnion and chorion layers of the placenta tissue are then carefully separated. In one aspect, the materials and equipment used in this procedure include a processing tray, 18% saline solution, sterile 4×4 sponges, and two sterile Nalgene jars. The placenta tissue is then closely examined to find an area (typically a corner) in which the amnion layer can be separated from the chorion layer. The amnion appears as a thin, opaque layer on the chorion.

Prior to removal of the epithelium, the fibroblast layer is identified by gently contacting each side of the membrane with a piece of sterile gauze or a cotton tipped applicator. The fibroblast layer will stick to the test material. The amnion is placed into processing tray fibroblast layer down. Using a blunt instrument, a cell scraper or sterile gauze, any residual blood is also removed. This step must be done with adequate care, again, so as not to tear the amnion or chorion tissues. The cleaning of the amnion is complete once the amnion tissue is smooth and opaque-white in appearance. If the amnion tissue is cleaned too much, the jelly-like fibroblast layer can be removed. Any areas of the amnion cleaned too aggressively and appear clear will be unacceptable and will ultimately be discarded.

Removal of Epithelium Layer from Amnion (Step 135)

The epithelium layer present on the amnion is substantially removed in order to expose the basement layer of the amnion. The significance of removing the epithelium layer is described below. The term "substantially removed" with respect to the amount of epithelium removed is defined herein as removing greater than 90%, greater than 95%, or greater than 99% of the epithelial cells from the amnion. The presence or absence of epithelial cells remaining on the amnion layer can be evaluated using techniques known in the art. For example, after removal of the epithelial cell layer, a representative tissue sample from the processing lot is placed onto a standard microscope examination slide. The tissue sample is then stained using Eosin Y Stain and evaluated as described below. The sample is then covered and allowed to stand. Once an adequate amount of time has passed to allow for staining, visual observation is done under magnification.

The epithelium layer can be removed by techniques known in the art. For example, the epithelium layer can be scraped off of the amnion using a cell scraper. Other techniques include, but are not limited to, freezing the membrane, physical removal using a cell scraper, or exposing the epithelial cells to nonionic detergents, anionic detergents, and nucleases. The de-epithelialized tissue is then evaluated to determine that the basement membrane has not been compromised and remains intact. This step is performed after completion of the processing step and the tissue has been dehydrated as described in the next section. For example, a representative sample graft is removed for microscopic analysis. The tissue sample is place onto a standard slide and 100 µl of Eosin Y stain is applied to the sample and allowed to set. The tissue sample is then examined under magnification. Cellular material will stain dark indicating the presence of cells. If no stained cells are present, de-epithelization has been achieved.

Chemical Decontamination (Step 140)

The amnion is then placed into a sterile Nalgene jar for the next step for additional cleaning If the chorion is to be recovered and processed further, it too is placed in its own sterile Nalgene jar for additional cleaning If the chorion is not to be kept or used further, it can be discarded in an appropriate biohazard container. In one aspect, the following procedure can be used to clean the amnion.

Each Nalgene jar is aseptically filled with 18% saline hypertonic solution and sealed (or sealed with a top). The jar is then placed on a rocker platform and agitated for between 30 and 90 minutes, which further cleans the tissue of contaminants. If the rocker platform was not in the critical environment (e.g., the manufacturing hood), the Nalgene jar is returned to the controlled/sterile environment and opened. Using sterile forceps or by aseptically decanting the contents, the tissue is gently removed from the Nalgene jar containing the 18% hyperisotonic saline solution and placed into an empty Nalgene jar. This empty Nalgene jar with the tissue is then aseptically filled with a pre-mixed antibiotic solution. Preferably, the premixed antibiotic solution is comprised of a cocktail of antibiotics, such as Streptomycin Sulfate and Gentamicin Sulfate. Other antibiotics, such as Polymixin B Sulfate and Bacitracin, or similar antibiotics now available or available in the future, are also suitable. Additionally, it is preferred that the antibiotic solution be at room temperature when added so that it does not change the temperature of or otherwise damage the tissue. This jar or container containing the tissue and antibiotics is then sealed or closed and placed on a rocker platform and agitated for, preferably, between 60 and 90 minutes. Such rocking or agitation of the tissue within the antibiotic solution further cleans the tissue of contaminants and bacteria.

Again, if the rocker platform was not in the critical environment (e.g., the manufacturing hood), the jar or container containing the tissue and antibiotics is then returned to the critical/sterile environment and opened. Using sterile forceps, the tissue is gently removed from the jar or container and placed in a sterile basin containing sterile water or normal saline (0.9% saline solution). The tissue is allowed to soak in place in the sterile water/normal saline solution for at least 10 to 15 minutes. The tissue may be slightly agitated to facilitate removal of the antibiotic solution and any other contaminants from the tissue. After at least 10 to 15 minutes, the tissue is ready to be dehydrated and processed further.

In the case when the chorion is to be used, the following exemplary procedure can be used. After separation of the chorion from the amnion and removal of clotted blood from the fibrous layer, the chorion is rinsed in 18% saline solution for 30 min. During the first rinse cycle, 18% saline is heated in a sterile container using laboratory heating plate such that the solution temperature is approximately 48° C. The solution is decanted, the chorion tissue is placed into the sterile container, and decanted saline solution is poured into the container. The container is sealed and placed on rocker plate and agitated for 1 hour. After 1 hour agitation bath, remove the tissue and place the tissue into second heated agitation bath for an additional 1 hour rinse cycle. Next, the chorion tissue is placed into 200 ml of 0.5% Triton-X wash solution. The container is sealed and agitated without heat for 2 hours. The tissue is next washed with deionized water (250 ml of DI water×4) with vigorous motion for each rinse. The tissue is removed and placed into a container of 1×PBS w/EDTA solution. The container is sealed and agitated for 1 hour at controlled temperature for 8 hours. The tissue is removed and rinsed using sterile water. A visual inspection was performed to remove any remaining discolored fibrous blood material from the membrane. Membrane should have a cream white visual appearance with no evidence of brownish discoloration.

Preparation of Tissue Graft and Dehydration (Step 150)

After removal of the epithelium layer, the amnion is ready to be used to produce the tissue graft. In one aspect, the amnion layer is laid on a suitable drying fixture, where the exposed basement membrane is adjacent to the surface of the drying fixture. In other aspects, the amnion can be placed on the surface of the drying fixture such that the exposed basement membrane is facing up. The drying fixture is preferably sized to be large enough to receive the amnion tissue, fully, in laid out, flat fashion. In one aspect, the drying fixture is made of Teflon or of Delrin, which is the brand name for an acetal resin engineering plastic invented and sold by DuPont and which is also available commercially from Werner Machine, Inc. in Marietta, Ga. Any other suitable material that is heat and cut resistant, capable of being formed into an appropriate shape to receive wet tissue and to hold and maintain textured designs, logos, or text can also be used for the drying fixture. It is desirable that the amnion tissue be placed on the drying fixture so that it completely covers as many "product spaces" (as explained hereinafter) as possible.

Figure 5:
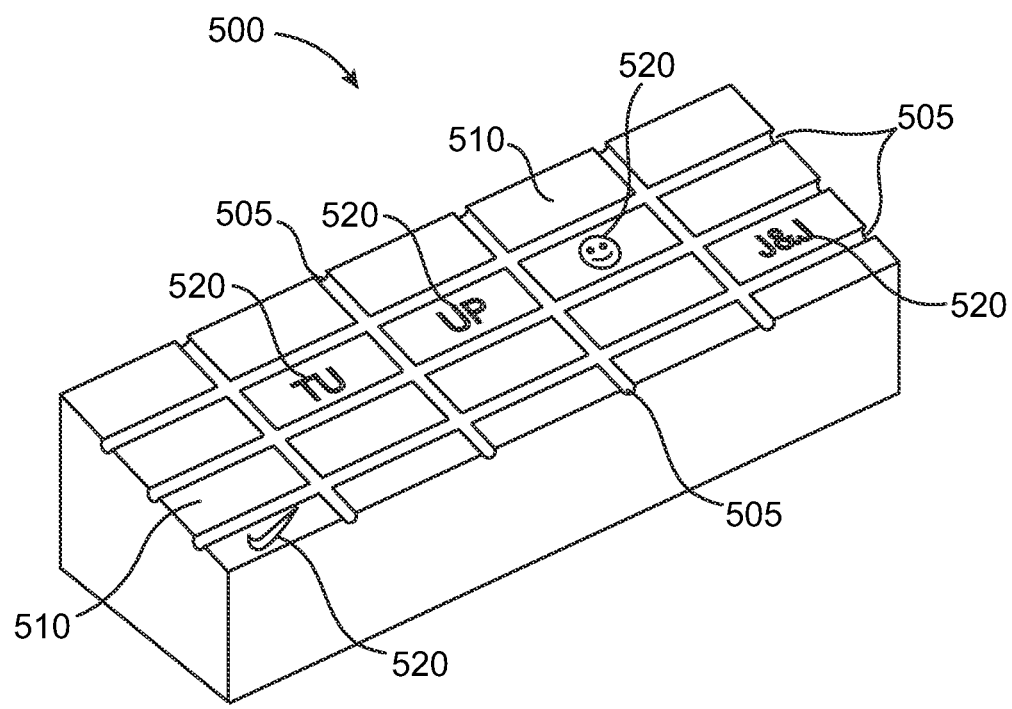
FIG. 5 is a perspective view of an exemplary drying fixture for making the tissue grafts described herein.

In one aspect, similar to that shown in FIG. 5, the receiving surface of the drying fixture 500 has grooves 505 that define the product spaces 510, which are the desired outer contours of the tissue after it is cut and of a size and shape that is desired for the applicable surgical procedure in which the tissue will be used. For example, the drying fixture can be laid out so that the grooves are in a grid arrangement. The grids on a single drying fixture may be the same uniform size or may include multiple sizes that are designed for different surgical applications. Nevertheless, any size and shape arrangement can be used for the drying fixture, as will be appreciated by those skilled in the art. In another embodiment, instead of having grooves to define the product spaces, the drying fixture has raised ridges or blades.

Within the "empty" space between the grooves or ridges, the drying fixture can include a slightly raised or indented texture in the form of text, logo, name, or similar design 520. This textured text, logo, name, or design can be customized. When dried, the tissue will mold itself around the raised texture or into the indented texture—essentially providing a label within the tissue itself. Preferably, such texture/label can be read or viewed on the tissue in only one orientation so that, after drying and cutting, an end user (typically, a clinician) of the dried tissue will be able to tell the stromal side from the basement side of the dried tissue. The reason this is desired is because, during a surgical procedure, it is desirable to place the allograft in place, with basement side down or adjacent the native tissue of the patient receiving the allograft. FIG. 5 illustrates a variety of marks, logos, and text 520 that can be included within the empty spaces 510 of the drying fixture 500. Typically, a single drying fixture will include the same design or text within all of the empty spaces; however, FIG. 5 shows, for illustrative purposes, a wide variety of designs that can be included on such drying fixtures to emboss each graft.

Figure 6:
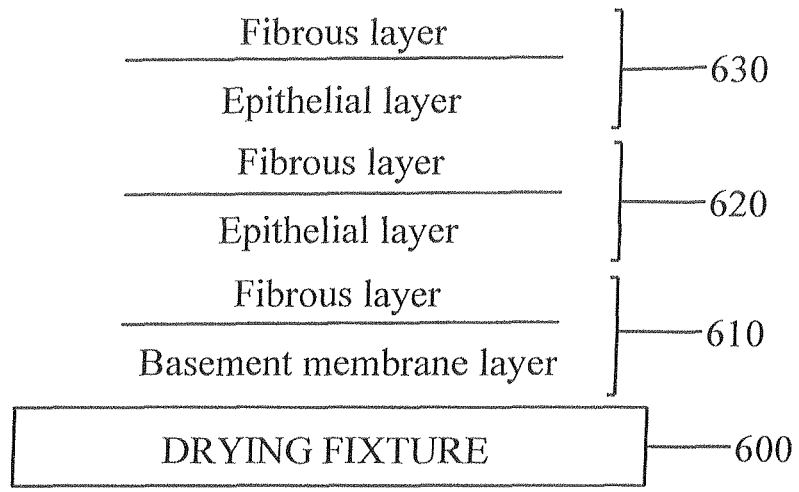
FIGS. 6-9 are representative side views of different tissue grafts described herein.

After the layer of amnion with substantially no epithelial cells on the surface of the basement membrane has been applied to the drying fixture, one or more membranes can applied to the base amnion layer to produce the tissue graft. FIGS. 6-9 depict numerous examples of multi-laminated tissue grafts produced by the methods described herein. Referring to FIG. 6, amnion layer 610 is applied to the surface of the drying fixture 600, where the basement membrane 605 is adjacent to the surface of the drying fixture 600. Two additional amnion layers 620 and 630 are applied to amnion 610. In this aspect, the fibrous layer of each amnion layer acts as an adhesive for the next layer. Thus, the fibrous layer of amnion 610 adheres to the epithelial layer of amnion 620. It is important to note that when multiple amnion layers are used, it is not necessary to remove the epithelial cells from the basement membrane for those layers that are not in direct contact with host cells. Although in this aspect, the fibroblast layer is used to adhere the membranes together, other techniques and materials such as, for example, fibrin glue, gelatin, photochemical techniques, and suturing can be used to produce the multi-laminated tissue graft.

Figure 7:
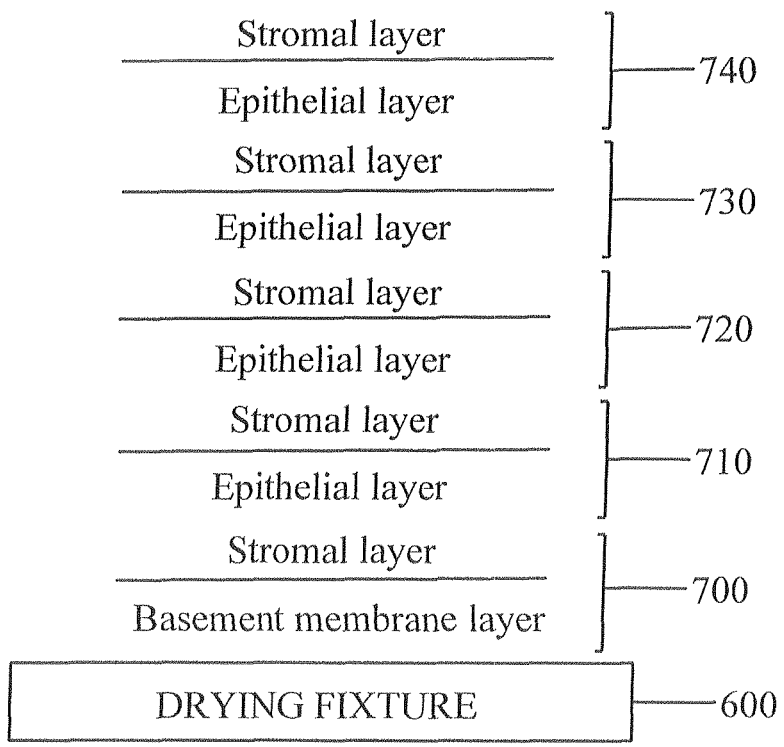
Figure 8:
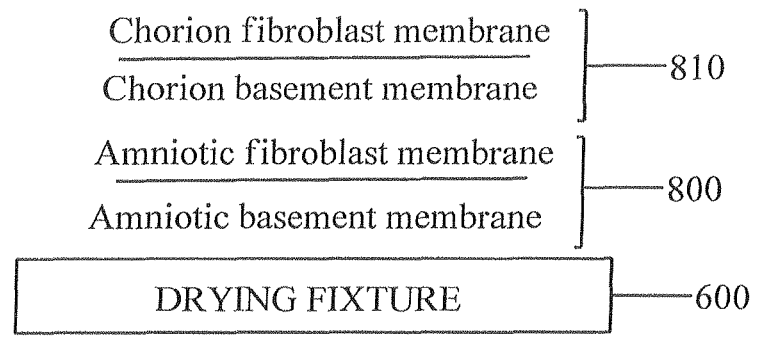

FIGS. 7 and 8 depict additional features of the multi-layered tissue graft. Referring to FIG. 7, amnion layer 700 minus the epithelial layer is applied to drying fixture 600. Four additional amnion layers (710-740) are then applied to the amnion layer 700. In FIG. 8, amnion layer 800 minus the epithelial layer is applied to drying fixture 600, and chorion layer 810 is applied to the amnion layer 800.

Figure 9:
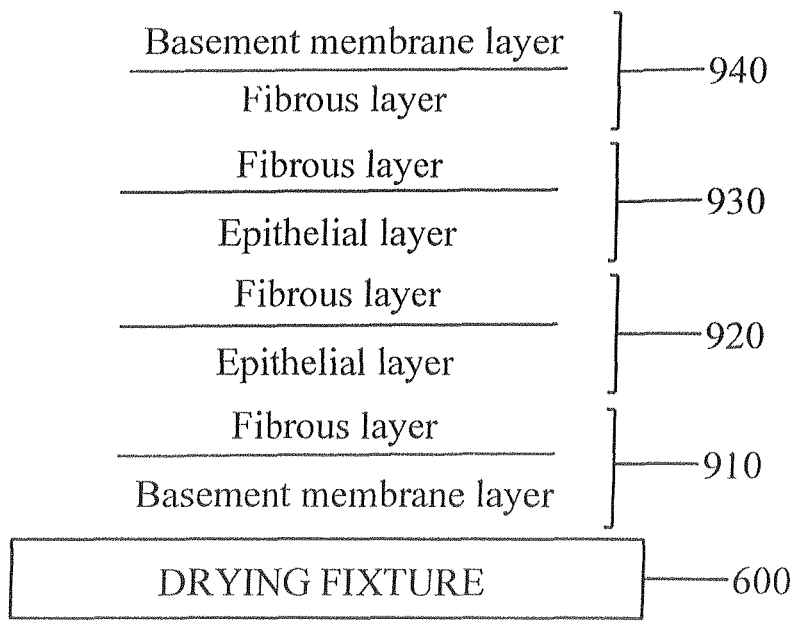

In another aspect, it is also contemplated that the multi-layered tissue graft can be composed of one or more membranes sandwiched between two amnion membranes with the amnion tissue with its epithelial layer removed exposing the basement membrane of the amnion tissue to host cells. This aspect is depicted in FIG. 9, where amnion layers 920 and 930 are sandwiched between amnion layers 910 and 940 (no epithelial layer).

Although FIGS. 6-9 depict the use of amnion and chorion to produce the multi-layered tissue graft, other biodegradable biologically compatible materials can be used in place of chorion to form a multi-layered amnion composite membrane. Examples of such materials include, but are not limited to, allograft pericardium, allograft acellular dermis, amniotic membrane (i.e., both amnion and chorion), Wharton's jelly, purified xenograft Type-1 collagen, biocellulose polymers or copolymers, biocompatible synthetic polymer or copolymer films, purified small intestinal submucosa, bladder acellular matrix, cadaveric fascia, or any combination thereof.

The actual number of layers will depend upon the surgical need and procedure with which the tissue graft is designed to be used for. For example, in periodontal applications such as root coverage procedures, a single membrane that is between 20-50 μm in thickness to multilayer tissue grafts having a thickness up to 2 mm can be used. In one aspect, the number of membranes laminated to the base amnion tissue with substantially all of the epithelial cells removed can be one, two, five and or ten, with the ultimate number of layers dependent of the type of membrane used, and the expected indication for use.

The multi-layered tissue grafts described herein are thicker and stronger than a single layer of base amnion. The base amnion may have handling limitations. In general, tissue grafts are cut to size to match the morphology of the wound, placed on or within the wound, and if desired, can be held in place with sutures. If left unsupported, the base amnion tissue may fall over itself, and may bunch together. Moreover, the native amnion tissue may be unable to hold sutures. Sutures may tear the tissue during placement, and may be knocked free by the patient. These issues make trimming, placement, and securing a single layer of base amnion tissue less than ideal for the medical professional.

Once the tissue graft is placed on the drying fixture, in one aspect, the drying fixture is placed in a sterile Tyvex (or similar, breathable, heat-resistant, and sealable material) dehydration bag and sealed. Such a breathable dehydration bag prevents the tissue from drying too quickly and prevents cross-contamination, when multiple donors are dehydrated in the oven at the same time. If multiple drying fixtures are being processed simultaneously, each drying fixture is either placed in its own Tyvex bag or, alternatively, placed into a suitable mounting frame that is designed to hold multiple drying frames thereon and the entire frame is then placed into a larger, single sterile Tyvex dehydration bag and sealed.

The Tyvex dehydration bag containing the one or more drying fixtures is then placed into an oven or incubator (vacuum or non-vacuum) that has been preheated to approximately 35 to 50° C. The Tyvex bag remains in the oven for between 30 and 120 minutes, although approximately 45 minutes at a temperature of approximately 45° C. appears to be ideal to dry the tissue sufficiently but without over-drying the tissue. The specific temperature and time for any specific oven will need to be calibrated and adjusted based on other factors including altitude, size of the oven, accuracy of the oven temperature, material used for the drying fixture, number of drying fixtures being dried simultaneously, whether a single or multiple frames of drying fixtures are dried simultaneously, and the like. In one aspect, the dehydration recordation form, similar to that shown in FIG. 4, can be completed at the end of the dehydration process.

In certain aspects the membrane is not physically altered except for final cutting and packaging (step 160). When completed, the processed tissue graft has a semi-transparent appearance with a whitish coloration. The tissue is pliable to withstand bending and sizing in its dry, non-hydrated state. The tissue grafts described herein can be stored at room temperature for extended periods of time.

Figure 10:
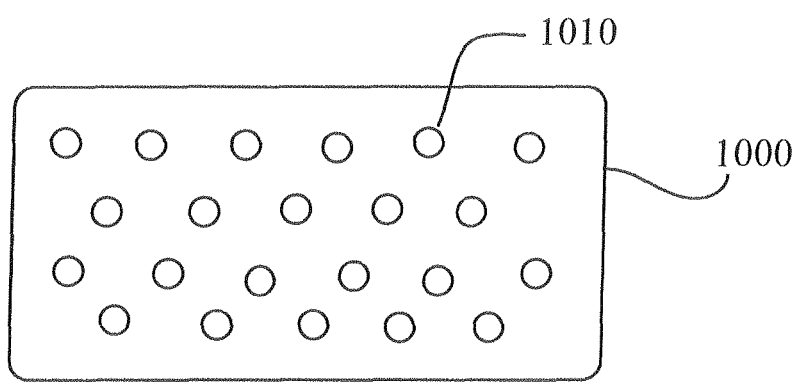
FIG. 10 is a top view of a tissue graft with perforations.

In certain aspects, after the dehydration phase, the tissue graft is perforated using a small gauge needle, or punch to produce a mesh-type configuration, as shown in FIG. 10, where a plurality of holes 1010 are present in graft 1000. The size and spacing of the holes can vary depending upon the application. In one aspect, the holes have a diameter from (0.2 mm-2.0 mm or 0.2 mm to 0.5 mm) and are spaced from 1 mm to 5 mm or 2 mm to 4 mm apart. The holes may facilitate cell migration and provide for the passage of blood and other factors to the opposite side of the graft, which ultimately enhances wound healing. For example, in several perioplastic procedures, the membrane is placed directly onto the exposed root of the tooth. Here, the tooth surface does not supply a source of blood and the holes provide a source of blood and other factors to the side of the membrane that is in direct contact with the tooth surface. In multi-layered products, the holes may allow for a more rapid and even distribution of wound healing agents which may be applied and or adsorbed onto prior to implantation to further improve the regenerative potential of the treatment. When completed, the processed tissue graft has a semi-transparent appearance with a whitish coloration. The tissue is pliable to withstand bending and sizing in its dry, non-hydrated state. The tissue grafts described herein can be stored at room temperature for extended periods of time.

Cutting & Packaging (Step 160)

Once the tissue graft has been adequately dehydrated, the tissue graft is then ready to be cut into specific product sizes and appropriately packages for storage, terminal sterilization, and later surgical use. In one aspect, the Tyvex bag containing the dehydrated tissue is placed back into the sterile/controlled environment. The number of grafts to be produced is estimated based on the size and shape of the tissue on the drying fixture(s). An appropriate number of pouches, one for each tissue graft, are then also introduced into the sterile/controlled environment. The drying fixture(s) are then removed from the Tyvex bag.

If the drying fixture has grooves, then the following exemplary procedure is followed for cutting the tissue into product sizes. If the drying fixture is configured in a grid pattern, a #20 or similar straight or rolling blade is used to cut along each groove line in parallel. Then, all lines in the perpendicular direction are cut. Alternatively, if the drying fixture has raised edges or blades, then the following procedure is followed for cutting the tissue into product sizes. A sterile roller is used to roll across the drying fixture. Sufficient pressure must be applied so that the dehydrated tissue is cut along all of the raised blades or edges of the drying fixture.

After cutting, each tissue graft is placed in a respective "inner" pouch. The inner pouch, which preferably has a clear side and an opaque side, should be oriented clear side facing up. The tissue graft is placed in the "inner" pouch so that the texture in the form of text, logo, name, or similar design is facing out through the clear side of the inner pouch and is visible outside of the inner pouch. This process is repeated for each separate graft.

Each tissue graft is then given a final inspection to confirm that there are no tears or holes, that the product size (as cut) is within approximately 1 millimeter (plus or minus) of the specified size for that particular graft, that there are no noticeable blemishes or discoloration of the tissue, and that the textured logo or wording is readable and viewable through the "inner" pouch.

To the extent possible, oxygen is removed from the inner pouch before it is sealed. The inner pouch can be sealed in any suitable manner; however, a heat seal has shown to be effective. In one aspect, after packaging, the product is terminally sterilized by radiation, using gamma or electron beam sterilization with a target dose of 17.5 kGy. Next, each inner pouch is separately packaged in an "outer" pouch for further protection, storage, and shipment.

It should be noted that the above process does not require freezing of the tissue to kill unwanted cells, to decontaminate the tissue graft, or otherwise to preserve the tissue graft. The dehydrated tissue grafts described herein are designed to be stored and shipped at room or ambient temperature without need for refrigeration or freezing.

Product Release (Step 170)

Before the tissue graft is ready for shipment and release to the end user, all documentation related to manufacture, recovery and donor eligibility are reviewed and deemed acceptable by the quality assurance department and the medical director.

Appropriate labeling and chain of custody is observed throughout all of the above processes, in accordance with accepted industry standards and practice. Appropriate clean room and sterile working conditions are maintained and used, to the extent possible, throughout the above processes.

II. Applications of Tissue Grafts

These membranes are composed of at least one layer of amnion tissue where the epithelium layer has been substantially removed in order to expose the basement layer to host cells. By removing the epithelium layer, cells from the host can more readily interact with the cell-adhesion bio-active molecules located onto top and throughout the basement membrane. These grafts could be composed of one or several layers of amnion tissue, combined with chorion or other biocompatible membranes to form tissue grafts. The laminin structure of amnion tissue is nearly identical to that of native human oral mucosa tissue. They both include high level of laminin-5, a cell adhesion factor show to bind gingival epithelia-cells, throughout upper portions of the basement membrane. By creating amnion only, amnion chorion graft, or composite graft where amnion tissue forms the outer most layer of the membrane, the membranes described herein will be highly suited for use in regenerative procedures involving the oral mucosa. Due to the similarity of mucosa tissue found in oral cavity, nose, throat, vagina, and rectum, it should also be highly effective in regenerative procedures in those anatomical regions. Although the laminins found in the basement membrane do not adhere to dermis epithelia cells, and it is unknown if cells specific to another anatomical location my adhere to the laminins found it on the basement membrane of amnion tissue, the amnion based membranes could be effective in broad range of applications including the treatment of burns, chronic wounds, and as grafts in cardiovascular surgery These membranes can be soaked with a bioactive agent such as a solution composed of naturally occurring growth factors sourced from platelet concentrates, either using autologous blood collection and separation products, or platelet concentrates sourced from expired banked blood; bone marrow aspirate; stem cells derived from concentrated human placental cord blood stem cells, concentrated amniotic fluid stem cells or stem cells grown in a bioreactor; or antibiotics. Here, one or more membrane layers of the tissue graft absorb the bioactive agent. Upon application of the wet tissue graft with bioactive agent to the wound, the bioactive agent is delivered to the wound over time.

The tissue grafts are easy to handle and do not readily break. Additionally, the tissue may composed in such an manner to hold sutures, provide specific rates of resorption based on the requirements of the indication in which it is being used.

The tissue grafts described herein have numerous applications and can be used in a variety of procedures. For example, the tissue grafts can be used in the following perioplastic procedures including the treatment of recession defects, increasing gingival tissue height and width, increase the amount of attached gingival tissue at the gingival margin, and increase the zone of attached gingival tissue, elimination of a frenum pull, regeneration of lost patella tissue, repair of the Schneiderian membrane in the sinus cavity, soft tissue around dental implants, vestibuloplasty, and guided tissue regeneration. In oral surgery they could be used to improve soft tissue outcomes and grow new bone in guided bone regeneration procedures. In applications involving oral mucosa tissue treating mouth sores and oral lesions, and larger replace larger amounts of mucosa tissue lost through disease or traumatic injury. These same membranes could also be used in reconstructive procedures where the tissue is composed of mucosa including in ear, nose, and throat, urogynecology, and surgical procedures involving the rectum and anus.

Methods for using the tissue grafts herein in periodontal applications are provided in the Examples.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Evaluation of Tissue Grafts to Repair Gingival Recession Defects

Tissue grafts composed of (5) layers of amniotic membrane with (1) each layer having intact epithelium and (2) the epithelial layer removed from the first amnion layer to expose the basement layer were evaluated. The epithelial layer was removed using a specialized instrument (custom cell scraper) according to SOP# 220.125, "Removal of the epithelial cell layer for de-epithelialized products". This procedure would allow for complete removal of the epithelial cell layer and exposure of the basement membrane. After removal of the epithelial cell layer, a representative tissue sample from the processing lot is placed onto a standard microscope examination slide. The tissue sample is then stained using Eosin Y Stain. The sample is then covered and allowed to stand. Once an adequate amount of time has passed to allow for staining, visual observation is done under magnification. The presence of cells and cellular material will appear darker than the areas which have been de-epithelialized.

A total of (10) consenting patients were implanted with the tissue grafts under initial design specifications. Patient # 1 of the case study evaluation was diagnosed with a Miller's Class I recession defect resulting in surgical decision. The patient displayed a pre-operative recession defect measuring 3 mm at tooth site # 5 in the maxillary region. Standard surgical techniques were employed with tissue graft placement (with epithelium) and closure technique. The exposed basement membrane was applied to the gingival, with the fibroblast layer attached to the tooth. Post-operative observations revealed soft tissue closure (flap) recession and soft tissue non-attachment at the (1) week post-operative interval.

After post-operative evaluation of patient #1, an assessment was made to address the soft tissue non-attachment. The cause of non-attachment was due to an interaction of the intact epithelial layer on the tissue graft with the migration of the patient's oral epithelial layer, which extends from the free gingival margin (FGM) to the gingival sulcus (GS). The interaction of the two epithelial tissue surfaces resulted in non-attachment.

Revision surgery was scheduled for patient # 1 following the observational follow-up visit. A repeat procedure at the same surgical site using the tissue graft without the epithelial layer was scheduled. The epithelial layer was manually removed intraoperatively using a hand scalpel blade. At the 8 week post-operative interval, patient # 1 showed good soft tissue attachment with no evidence of soft tissue flap recession. Post-operative recession measurements were taken and documented at 1 mm. All subsequent grafts used in the case study evaluation were manually de-epithelialzed intraoperatively. The remaining patients enrolled in the case study evaluation exhibited no visual evidence of soft tissue non-attachment and no evidence of soft tissue flap recession.

A second study was conducted to confirm the observations and comparing grafts prepared using the methods described herein (control material with no epithelial layer) and grafts that were prepared without removing the epithelial layer (test material). All patients were diagnosed with Miller Class I/II recession defects. Success was determined if the patients obtained 90% root coverage. A total seven patients (15 teeth) were treated with the test material and nine patients (13 teeth) with the control material. In the control group, 8 of the 13 (62%) teeth treated were deemed successful whereas only 2 of the 15 (13%) teeth treated with the test material had a successful outcome. Although this study was not powered for statistical significance, the date obtained clearly showed the presence of the epithelial layer resulted in a lower rate of success.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed is:

1. A dehydrated amnion membrane comprising a non-fixated, dehydrated modified amnion membrane wherein the modified amnion membrane has a first side which is an exposed basement membrane substantially free of epithelium cells and a second side which is a fibroblast cellular layer, and wherein the amnion membrane is dehydrated on or in a heated drying fixture.

2. The dehydrated amnion membrane of claim 1 wherein greater than 90% of the epithelium cells are removed from the amnion membrane.

3. The dehydrated amnion membrane of claim 1 wherein greater than 95% of the epithelium cells are removed from the amnion membrane.

4. The dehydrated amnion membrane of claim 1 wherein greater than 99% of the epithelium cells are removed from the amnion membrane.

5. The dehydrated amnion membrane of claim 1 wherein said amnion membrane is laminated to one or more additional layers selected from chorion, amnion, allograft pericardium, allograft acelluar dermis, amniotic membrane, Wharton's jelly, purified xenograft Type-1 collagen, biocellulose polymers or copolymers, biocompatible synthetic polymer or copolymer films, purified small intestinal submucosa, bladder acellular matrix, cadaveric fasia, or a combination thereof.

6. The dehydrated amnion membrane of claim 1, wherein the amnion membrane is dehydrated at a temperature between 35° C. and 50° C.

* * * * *